US010195242B2

(12) United States Patent
Hale et al.

(10) Patent No.: US 10,195,242 B2
(45) Date of Patent: Feb. 5, 2019

(54) THERAPEUTIC COMPOUNDS

(71) Applicant: Wintermute Biomedical, Inc., Missoula, MT (US)

(72) Inventors: Weston J. Hale, Missoula, MT (US); Thomas F. Rau, Stevensville, MT (US)

(73) Assignee: Wintermute Biomedical, Inc., Missoula, MT (US)

( * ) Notice: Subject to any disclaimer, the term of this patent is extended or adjusted under 35 U.S.C. 154(b) by 349 days.

(21) Appl. No.: 14/760,778

(22) PCT Filed: Jan. 27, 2014

(86) PCT No.: PCT/US2014/013120
§ 371 (c)(1),
(2) Date: Jul. 14, 2015

(87) PCT Pub. No.: WO2014/117056
PCT Pub. Date: Jul. 31, 2014

(65) Prior Publication Data
US 2015/0366925 A1 Dec. 24, 2015

Related U.S. Application Data
(60) Provisional application No. 61/757,058, filed on Jan. 25, 2013.

(51) Int. Cl.
| | |
|---|---|
| A61K 36/00 | (2006.01) |
| A61K 36/36 | (2006.01) |
| A61K 36/70 | (2006.01) |
| A61K 36/708 | (2006.01) |
| A61K 8/97 | (2017.01) |
| A61K 8/36 | (2006.01) |
| A61K 8/44 | (2006.01) |
| A61Q 17/00 | (2006.01) |
| A61K 31/198 | (2006.01) |
| A61K 31/201 | (2006.01) |

(52) U.S. Cl.
CPC ............ *A61K 36/708* (2013.01); *A61K 8/361* (2013.01); *A61K 8/44* (2013.01); *A61K 8/97* (2013.01); *A61K 31/198* (2013.01); *A61K 31/201* (2013.01); *A61Q 17/005* (2013.01)

(58) Field of Classification Search
None
See application file for complete search history.

(56) References Cited

U.S. PATENT DOCUMENTS

| | | | |
|---|---|---|---|
| 4,150,052 | A | 4/1979 | Watson et al. |
| 5,766,614 | A | 6/1998 | Yong |
| 6,841,174 | B2 | 1/2005 | Shalaby et al. |
| 7,288,265 | B1 * | 10/2007 | Rolf ............. A61K 9/7038 424/443 |
| 2007/0258913 | A1 | 11/2007 | Rossel |
| 2009/0068128 | A1 | 3/2009 | Waddington |
| 2010/0111879 | A1 * | 5/2010 | Tamarkin ........... A61K 8/046 424/45 |
| 2012/0328544 | A1 | 12/2012 | Stockel et al. |
| 2016/0066578 | A1 | 3/2016 | Ala'Aldeen et al. |

FOREIGN PATENT DOCUMENTS

| | | |
|---|---|---|
| CN | 1969984 | 5/2007 |
| CN | 101991726 A * | 3/2011 |
| CN | 102178842 B | 9/2011 |
| EP | 1595936 | 10/2005 |
| JP | H11-269034 | 10/1999 |
| JP | 2000-281528 | 10/2000 |
| JP | 2002-114670 | 4/2002 |
| WO | WO2004/026840 A1 | 4/2004 |
| WO | WO2005/049553 A1 | 6/2005 |
| WO | WO2005/123101 A1 | 12/2005 |
| WO | WO2006/046025 A1 | 5/2006 |
| WO | WO2008111532 A1 * | 9/2008 |
| WO | WO2012/090205 A2 | 7/2012 |

OTHER PUBLICATIONS

Chung et al.; Rhein affects arylamine N-acetyltransferase activity in Helicobacter pylori from peptic ulcer patients; Journal of Applied Toxicology; 18(2); pp. 117-123; Mar. 1, 1998.
Diep et al.; Complete genome sequence of USA300, an epidemic clone of community-acquired meticillin-resistant *Staphylococcus aureus*; The Lancet; 367(9512); pp. 731-739; Mar. 4, 2006.
Handa et al.; (Ed); Extraction technologies for medicinal and aromatic plants; United Nations Industrial Development Organization and the International Centre for Science and High Technology, Trieste; 266 pages; (year of pub. sufficiently earlier than effective US filing date and any foreign priority date); 2008.
MacMicking et al.; Nitric oxide and macrophage function; Annual Review of Immunology; 15(1); pp. 323-350; Apr. 15, 1997.
Nakaki et al.; L-arginine-induced hypotension; The Lancet; 336(8716); pp. 696; Sep. 15, 1990.
Rattner et al.; Treatment of psoriasis with undecylenic acid by mouth; Journal of the American Medical Association; 146(12); pp. 1113-1115; Jul. 21, 1951.
Wrong; Undecylenic acid administered orally in the treatment of psoriasis; Can. Med. Assoc. J..; 63(6); pp. 543-545; Dec. 1950.
Wu et al.; Antimicrobial properties and toxicity of anthraquinones by microcalorimetric bioassay; Chinese Journal of Chemistry; 24(1); pp. 45-50; Jan. 1, 2006.
Yu et al.; Global transcriptional response of *Staphylococcus aureus* to rhein, a natural plant product; Journal of Biotechnology; 135(3); pp. 304-308; Jun. 30, 2008.
Bourne et al., "Effect of Undecylenic Acid as a Topical Microbicide Against Genital Herpes Infection in Mince and Guinea Pigs," *Antiviral Res.* 40:139-144 (1999).

(Continued)

*Primary Examiner* — Christopher R Tate
*Assistant Examiner* — Randall Winston
(74) *Attorney, Agent, or Firm* — Shay Glenn LLP

(57) ABSTRACT

The invention features therapeutic compounds useful for the treatment of skin diseases (e.g., psoriasis and eczema), infections (microbial, viral, and fungal), and wounds (e.g., cuts and burns). The compounds of the invention include therapeutically-effective amounts of L-Arginine, undecylenic acid, and *Rheum Officinale* extract. The invention further provides for the administration of the therapeutic compounds to a patient (e.g., a human) suffering from a skin disease, infection, or wound.

9 Claims, 10 Drawing Sheets

(56) References Cited

OTHER PUBLICATIONS

Ding et al., "Screening for Novel Quorum-Sensing Inhibitors to Interfere with the Formation of *Pseudomonas aeruginosa* Biofilm," *J. Med. Microbiol.* 60:1827-1834 (2011).
Helms et al., "Natural Treatment of Chronic Rhinosinusitis," *Alternative Medicine Rev.* 11(3):196-207 (2006).
Li et al., "Potent In Vitro Antifungal Activities of Naturally-Occurring Acetylenic Acids," *Antimicrobial Agents and Chemotherapy* 52(7): 2442-2448 (2008).
McLain et al., "Undecylenic Acid Inhibits Morphogenesis of *Candida albicans*," *Antimicrobial Agents and Chemotherapy* 44(10):2873-2875 (2000).
Thurlow et al., "Functional Modularity of the Arginine Catabolic Mobil Element Contributes to the Success of USA300 Methicillin-Resistant *Staphylococcus aureus*," *Cell Host Microbe* 13(1):100-107 (2013).
Monograph, "Undecylenic Acid," *Alternative Medicine Rev.* 7(1):68-70 (2002).
Office Action from Japanese Patent Application No. 555373/2015, dated Apr. 4, 2017 (English Translation).
Office Action from Japanese Patent Application No. 555373/2015, dated Oct. 3, 2017 (English Translation).
European Search Report from European Patent Application No. 14742746, Published Jul. 28, 2016.
Angele et al.; L-arginine: a unique amino acid for improving depressed wound immune function following hemorrhage; European Surgical Research; 34(1-2); pp. 53-60; Jan.-Apr. 2002.
Atilano et al.; Wall teichoic acids of *Staphylococcus aureus* limit recognition by the *Drosophila* peptidoglycan recognition protein-SA to promote pathogenicity; Plos Pathogens; 7(12); ; 13 pages; e1002421; Dec. 1, 2011.
Brown et al.; Methicillin resistance in *Staphylococcus aureus* requires glycosylated wall teichoic acids; Proceedings of the National Academy of Sciences; 109(46); pp. 18909-18914; (Author Manuscript); Nov. 13, 2012.
Brown et al.; *Staphylococcus aureus* and Bacillus subtilis W23 make polyribitol wall teichoic acids using different enzymatic pathways; Chemistry and Bilogy; 17(10); pp. 1101-1110; Oct. 29, 2010.
Diep et al.; The arginine catabolic mobile element and staphylococcal chromosomal cassette mec linkage: convergence of virulence and resistance in the USA300 clone of methicillin-resistant *Staphylococcus aureus*; The Journal of Infectious Diseases; 197(11); pp. 1523-1530; Jun. 1, 2008.
drugs.com; Rhubarb; 8 pages; retrieved from the internet (https://www.drugs.com/npp/rhubarb.html) on May 8, 2018.
Garcia-Sosa et al.; Chrysophanol, an antimicrobial anthraquinone from the root extract of colubrina greggii; Journal of the Mexican Chemical Society; 50(2); pp. 76-78; Jun. 2006.
Green et al.; Nitric oxide: cytokine-regulation of nitric oxide in host resistance to intracellular pathogens; Immunology Letter; 43(1-2); pp. 87-94; Dec. 1, 1994.
Lai et al.; Rhein induced apoptosis through the endoplasmic reticulum stress, caspase- and mitochondria-dependent pathways in SCC-4 human tongue squamous cancer cells; In Vivo; 23(2); pp. 309-316; Mar. 1, 2009.
Lee et al.; Synergistic effect of emodin in combination with ampicillin or oxacillin against methicillin-resistant *Staphylococcus aureus*; Pharmaceutical Bilogy; 48(11); pp. 1285-1290; Nov. 1, 2010.
MacMicking et al.; Identification of nitric oxide synthase as a protective locus against tuberculosis; Proceedings of the National Academy of Sciences; 94(10); pp. 5243-5248; May 13, 1997.
Morris; Enzymes of arginine metabolism; The Journal of Nutritiion; 134(10); pp. 2743S-2747S; Oct. 1, 2004.
Nelson; Undecylenic acid in the treatment of psoriasis and neurodermatitis; California Medicine; 74(1); pp. 17; Jan. 1951.
Seguin et al.; Induction of nitric oxide synthase protects against malaria in mice exposed to irradiated Plasmodium berghei infected mosquitoes: involvement of interferon gamma and CD8+ T cells; Journal of Experimental Medicine; 180(1); pp. 353-358; Jul. 1, 1994.
Shafran et al.; Topical undecylenic acid for herpes simplex labialis: a multicenter, placebo-controlled trial; Journal of Infectious Diseases; 176(1); pp. 78-83; Jul. 1, 1997.
Testa et al.; Hydrolysis in drug and prodrug metabolism: Chemistry, Biochemistry, and Enzymology; Wiley-VCH, Zurich, Switzerland, 2003; 11 pages; retrieved from the interent (http://sutlib2.sut.ac.th/sut_contents/H89132.pdf); on May 8, 2018.

\* cited by examiner

THERAPEUTIC COMPOUNDS

CROSS-REFERENCE TO RELATED APPLICATIONS

This application is the National Stage of International Application No. PCT/US2014/013120, filed Jan. 27, 2014, which claims the benefit of the filing date of U.S. Provisional Patent Application Ser. No. 61/757,058, filed Jan. 25, 2013, the disclosures of which are incorporated by reference in their entirety.

STATEMENT REGARDING FEDERALLY SPONSORED RESEARCH OR DEVELOPMENT

Not Applicable.

BACKGROUND OF THE INVENTION

Bacterial infections of the skin and underlying tissue present a significant clinical treatment issue. These types of infections commonly involve Gram-positive bacteria that colonize on the skin and underlying tissue and symptoms can range from mild discomfort to death. Bacteria cause a number of skin conditions such as impetigo, cellulitis, boils, and acne. Deep tissue infections of surgical wounds or traumatic wounds can invade the blood stream leading to septicemia and death.

Currently, many skin infections that are caused by Gram-positive bacteria are aggressively treated with antibiotics. However, as strains of pathogenic bacteria develop antibiotic resistance mechanisms, it becomes crucial to develop novel therapies that inhibit bacterial growth without using traditional antibiotics. In recent years, the issue of bacterial antibiotic resistance has become much more recognized with the development of so-called 'superbugs' such as methicillin-resistant *Staphylococcus aureus* (MRSA) and vancomycin-resistant *enterococcus* (VRE). These bacteria are common skin pathogens that have developed significant antibiotic resistance. With the continued use of antibiotics in both humans and animals bred for consumption, many common strains of skin bacteria are developing widespread antibiotic resistance leading to a serious health care issues. Common bacteria that are implicated in skin infections are Methicillin resistant *Staphylococcus aureus*, *S. pyogenes* and *S. pneumoniae*, *E. faecalis* and *S. agalactiae*. As these bacteria colonize the skin they break down the epidermis, induce an inflammatory response, and if untreated, invade into deeper tissue causing cellulitis. In extreme cases the bacteria invade the circulatory system causing sepsis and possible death.

It has become evident to the medical community that novel treatments must be developed to address this issue. However, many pharmaceutical companies have not aggressively pursued the development of new, antimicrobial treatments for skin and wound infections.

SUMMARY OF THE INVENTION

In general, the present invention is based on the discovery of compounds that exhibit therapeutic properties when used to treat, e.g., skin infections or wounds. These therapeutic compounds can be used to treat or prevent a disease, condition, or symptom in a patient (e.g. a human) caused by an infection (e.g., a bacterial, fungal, viral, or parasitic skin infection) or to promote wound healing. Accordingly, in a first aspect, the invention provides as therapeutic compound containing L-Arginine, undecylenic acid, and *Rheum Officinale* extract, or a pharmaceutically acceptable salt thereof. In one embodiment, the amount of L-Arginine in the combination therapy is from about 5% w/v to 500% w/v. In another embodiment, the amount of undecylenic acid in the combination therapy is from about 2% v/v to 50% v/v. In a further embodiment, the amount of *Rheum Officinale* extract in the combination therapy is from about 0.025% w/v to 2.5% w/v. In another embodiment, the amount of L-Arginine is about 50% w/v, the amount of undecylenic acid is about 20% v/v, and the amount of *Rheum Officinale* extract is about 0.25% w/v. In all embodiments, the combination therapy can include a cooling or heating additive, such as menthol, or a pharmaceutically acceptable excipient, diluent, or carrier. In all embodiments, the compound may be optimized for topical application.

In a second aspect, the invention features a method of treating a patient, such as a human) suffering from a disease by administering to the patient a therapeutically effective amount of the compounds of the invention. In one embodiment, the patient suffers from, or is at risk of contracting, a skin disease such as acne, psoriasis, or eczema. In another embodiment, the patient suffers from an infection caused by a microbial, viral, or fungal agent. In a further embodiment, the patient suffers from, or is at risk of developing, a burn, cut, puncture, or abrasion wound. In all such embodiments, the patient is administered the therapeutic compound of the invention containing about 50% w/v L-Arginine, about 20% v/v undecylenic acid, and 0.25% w/v *Rheum Officinale* extract.

In a third aspect, the invention features a kit containing the therapeutic compound of the invention and instructions useful for administering the therapy to a patient in need thereof.

Further embodiments, features, and advantages of the present invention, as well as the structure and operation of the various embodiments of the present invention, are described in detail below with a reference to the accompanying drawings.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

As used herein, the singular form "a," "an," and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the terms below have the meanings indicated.

The term "acyl" as used herein, alone or in combination, refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(O)CH$_3$ group.

An "alkylcarbonyl" or "alkanoyl" group refers to an alkyl group attached to the parent molecular moiety through a carbonyl group. Examples of such groups include methyl-carbonyl and ethylcarbonyl. Examples of acyl groups include formyl, alkanoyl and aroyl.

The term "alkenyl" as used herein, alone or in combination, refers to a straight-chain or branched-chain hydrocarbon radical having one or more double bonds optionally substituted and containing from 2 to 20, preferably 2 to 6, carbon atoms. Alkenyl refers to a carbon-carbon double bond system attached at two or more positions such as ethenylene [(—CH=CH—), (—C::C—)]. Examples of alkenyl radicals include ethenyl, propenyl, 2-methylpropenyl, 1,4-butadienyl and the like.

The term "alkoxy" as used herein, alone or in combination, refers to an alkyl ether radical, optionally substituted wherein the term alkyl is as defined below. Examples of alkyl ether radicals include methoxy, ethoxy, n-propoxy, isopropoxy, n-butoxy, iso-butoxy, sec-butoxy, tert-butoxy, and the like.

The term "alkyl" as used herein, alone or in combination, refers to a straight-chain or branched-chain alkyl radical optionally substituted containing from 1 to 20 and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like.

The term "alkylamino" as used herein, alone or in combination, refers to an alkyl group optionally substituted attached to the parent molecular moiety through an amino group. Alkylamino groups may be mono- or dialkylated, forming groups such as, for example, N-methylamino, N-ethylamino, N,N-dimethylamino, N,N-ethylmethylamino and the like.

The term "alkylthio" as used herein, alone or in combination, refers to an alkyl thioether (R—S—) radical wherein the term alkyl is as defined above and wherein the sulfur may be singly or doubly oxidized. Examples of alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl" as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynyl" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The term "amido" as used herein, alone or in combination, refer to an amino group as described below attached to the parent molecular moiety through a carbonyl group, or vice versa.

The term "amino" as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl" as used herein, alone or in combination, means a carbocyclic aromatic system containing one, two or three rings wherein such rings may be attached together in a pendent manner or may be fused optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

The terms "arylalkyl" or "aralkyl" as used herein, alone or in combination, refers to an aryl group attached to the parent molecular moiety through an alkyl group.

The term "aryloxy" as used herein, alone or in combination, refers to an aryl group attached to the parent molecular moiety through an oxygen atom.

The term "polyether radical" means a polyether radical containing from 2 to 6 carbon atoms interrupted with at least one oxygen atom, such as methoxymethyl, ethoxymethyl or methoxyethoxymethyl radicals or methoxyethyl.

The terms "benzo" and "benz" as used herein, alone or in combination, refer to the divalent radical $C_6H_4=$ derived from benzene. Examples include benzothiophene and benzimidazole.

The terms "carbamate" and "carbamoyl" as used herein, alone or in combination, refers to an ester of carbamic acid (—NHCOO—) which may be attached to the parent molecular moiety from either the nitrogen or acid end, and which may be optionally substituted as defined herein.

The term "carbonyl" as used herein, when alone includes formyl [—C(O)H] and in combination is a —C(O)— group.

The term "carboxy" as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "chemical stability" according to the invention means that the content exhibits very little variation with respect to the initial content, namely, that the variation in content of active principle at the time T should not be less than 90% to more particularly than 95% of the initial content at T0.

The term "cyano" as used herein, alone or in combination, refers to —CN.

The term "cycloalkyl" or, alternatively, "carbocycle", as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo-fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester" as used herein, alone or in combination, refers to a carboxy group bridging two moieties linked at carbon atoms.

The term "ether" as used herein, alone or in combination, refers to an oxygen atom bridging two moieties linked at carbon atoms.

The terms "halo" or "halogen" as used herein, alone or in combination, refers to fluorine, chlorine, bromine, or iodine.

The term "haloalkyl" as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CHF—), difluoromethylene (—CF$_2$—), chloromethylene (—CHCl—) and the like.

The term "heteroalkyl" as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected, from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl" as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, benzimidazolyl, quinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocyclyl", as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocyclyl" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocyclyl groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazoyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups may be optionally substituted unless specifically prohibited.

The term "hydroxyl" as used herein, alone or in combination, refers to —OH.

The phrase "in the main chain" refers to the longest contiguous or adjacent chain of carbon atoms starting at the point of attachment of a group to the compounds of this invention.

The phrase "linear chain of atoms" refers to the longest straight chain of atoms independently selected from carbon, nitrogen, oxygen and sulfur.

The term "lower" as used herein, alone or in combination, means containing from 1 to and including 6 carbon atoms.

The term "negatively-charged ion" as used herein, refers to any negatively-charged ion or molecule, either inorganic (e.g., Cl$^-$, Br$^-$, I$^-$) or organic (e.g., TsO— (i.e., tosylate)).

The term "nitro" as used herein, alone or in combination, refers to —NO$_2$.

The term "perhaloalkyl" as used herein, alone or in combination, refers to an alkyl group where all of the hydrogen atoms are replaced by halogen atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstitutedsilyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the direction they rotate plane polarized light. There are two types of optical isomers. The first type of optical isomers are compounds that are mirror images of one another but cannot be superimposed on each other. These isomers are called "enantiomers." The second type of optical isomers are molecules that are not mirror images but each molecule rotates plane polarized light and are considered optically-active. Such molecules are called "diastereoisomers." Diastereoisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "imaging agent" as used herein refers to any moiety useful for the detection, tracing, or visualization of a compound of the invention when coupled thereto. Imaging agents include, e.g., an enzyme, a fluorescent label (e.g., fluorescein), a luminescent label, a bioluminescent label, a magnetic label, a metallic particle (e.g., a gold particle), a nanoparticle, an antibody or fragment thereof (e.g., a Fab, Fab', or F(ab')$_2$ molecule), and biotin. An imaging agent can be coupled to a compound of the invention by, for example, a covalent bond, ionic bond, van der Waals interaction or a hydrophobic bond. An imaging agent of the invention can be a radiolabel coupled to a compound of the invention, or a radioisotope incorporated into the chemical structure of a compound of the invention. Methods of detecting such imaging agents include, but are not limited to, positron emission tomography (PET), X-ray computed tomography (CT) and magnetic resonance imaging (MRI).

The phrase "therapeutically effective" is intended to qualify the amount of active ingredients used in the treatment of a disease or disorder. This amount will achieve the goal of reducing or eliminating the disease or disorder.

The term "therapeutically acceptable" refers to those compounds (or salts, esters, prodrugs, tautomers, zwitterionic forms, etc. thereof) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means mammals and non-mammals. Mammals means any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "patient" does not denote a particular age or sex.

The term "prodrug" refers to a compound that is made more active in vivo. Certain compounds of the present invention may also exist as prodrugs, as described in *Hydrolysis in Drug and Prodrug Metabolism: Chemistry, Biochemistry, and Enzymology*, Testa, Bernard and Wiley-VHCA, Zurich, Switzerland 2003. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bio-available by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug is a compound that is administered as an ester (the "prodrug"), but then is metabolically hydrolyzed to the carboxylic acid, the active entity. Additional examples include peptidyl derivatives of a compound.

The compounds of the invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Stahl, P. Heinrich, *Pharmaceutical Salts: Properties, Selection, and Use*, Wiley-VCHA, Zurich, Switzerland (2002).

The term "therapeutically acceptable salt" as used herein, represents salts or zwitterionic forms of the compounds of the present invention which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

DETAILED DESCRIPTION OF THE INVENTION

Figure 1:
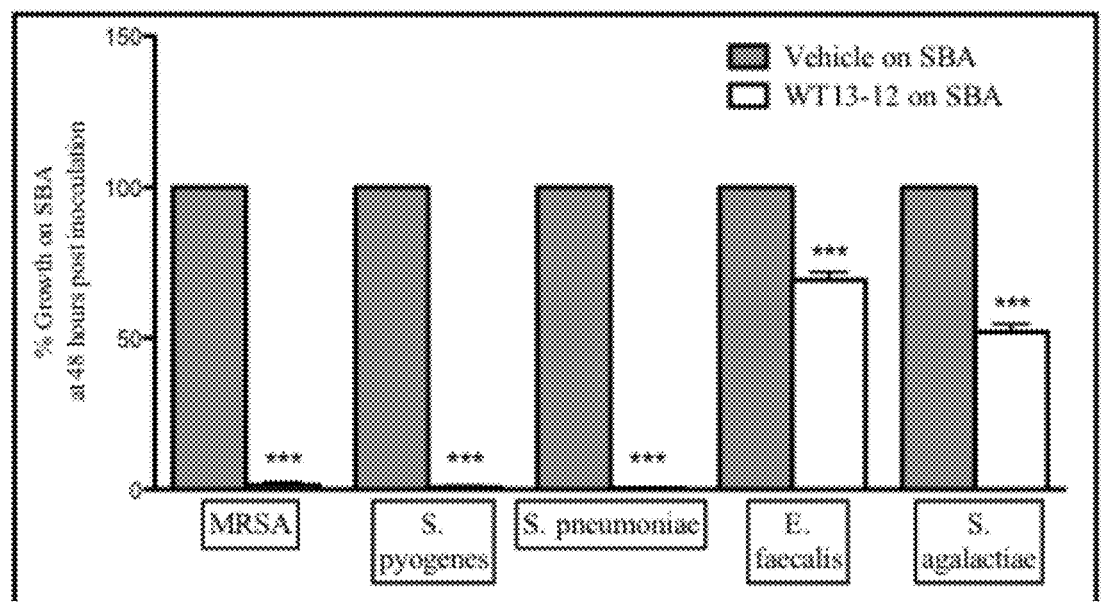
FIG. 1 is a bar graph showing the in vitro growth inhibition of five Gram-positive bacterial strains (MRSA, *S. pyogenes, S. pneumonia, E. faecalis,* and *S. agalactiae*) forty-eight hours after inoculation. Screening on SBA plates showed WT13-12 completely inhibited growth of MRSA, *S. pyogenes*, and *S. pneumonia*. WT13-12 also partially inhibited *E. faecalis* (30%) and *S. agalactiae* (48%) growth. Growth of bacteria in vehicle was set at 100% growth (uninhibited). All data was compared to vehicle in an unpaired, two-tailed T-test. n=4 test plates per group.

The combination therapies of the present invention are effective at inhibiting, e.g., bacterial, fungal and viral growth while at the same time aiding in wound healing. The combination therapies of the invention contain therapeutically effective amounts of L-Arginine, undecylenic acid and the extract of *Rheum Officinale* (Chinese rhubarb). The combination of these three components exerts a synergistic, not additive, biological mechanism of action. Furthermore, the inventors have found that the combination of these three compounds confers greater therapeutic benefit to a treated patient (e.g., a human) than the sequential administration of the individual compounds.

The combination therapies of the invention are useful for treating symptoms, conditions, and diseases caused by, e.g., bacterial, fungal, or viral infections in a patient (e.g., a human). In one embodiment, a combination therapy is formulated for topical application to treat skin disorders, infections, or conditions such as, e.g., psoriasis, acne, and eczema. In another embodiment, a combination therapy is formulated for application to a wound site (e.g., burnt skin or tissue).

The invention features pharmaceutical preparations and the medicaments obtained therefrom. The methods and formulations to prepare the combination therapies of the invention are disclosed here and in the Examples.

*Rheum Officinale* Extract

Biologically active extracts of *Rheum Officinale* may be prepared according to standard methods known in the art, including, e.g., maceration, infusion, digestion, decoction, percolation, hot continuous extraction, aqueous alcoholic extraction by fermentation, counter-current extraction (sonication), and supercritical fluid extraction, as described by Handa et al, "Extraction Technologies for Medicinal and Aromatic Plants," United Nations Industrial Development Organization and the International Centre for Science and High Technology, Trieste (2008), incorporated herein by reference.

Additives

In some formulations of the combination therapies of the invention it may be appropriate or preferable to include additives that modify or improve the cosmetic qualities of the final product. For example, one or more further substances with a physiological cooling effect can be used as a component in a mixture according to the invention, are selected here from the following list: menthol and menthol derivatives (for example L-menthol, D-menthol, racemic menthol, isomenthol, neoisomenthol, neomenthol) menthylethers (for example (I-menthoxy)-1,2-propandiol, (I-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxyl)acetate, menthyl-(2-methoxyethoxyl)acetate, menthylpyroglutamate), menthylcarbonates (for example menthylpropyleneglycolcarbonate, menthylethyleneglycolcarbonate, menthytglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N.sup.alpha.-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005/049553, methanecarboxylic add-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric add-N-methylamide [WS23]), isopulegol or its esters (I-(−)-isopulegol, I-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840).

Alternatively, the combination therapies of the invention can include additives which cause a hot, sharp, tingly or prickly feeling on the skin or on the mucous membranes, in particular flavors with a heat-producing effect and/or sharp tasting compounds (sharp substances), as described in WO 2005/123101.

Compound Formulation and Administration

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid. The novel compounds described herein can be prepared in a form of pharmaceutically acceptable salts that will be prepared from nontoxic inorganic or organic bases including but not limited to aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally-occurring substituted amines, cyclic amines, and basic ion exchange resins, such as arginine, betaine, caffeine, choline, ethylamine, 2-diethylaminoethano, 1,2-dimethylaminoethanol, ethanolamine, ethylenediamine, N-ethyl-morpholine, N-ethylpiperidine, glucamine, glucosamine, histidine, hydroxylamine, isopropylamine, lysine, methylglucamine, morpholine, piperazine, piperidine, polyamine resins, procaine, purines, theobromine, triethylamine, trimethylamine, trishydroxylmethyl amino methane, tripropyl amine, and tromethamine.

If the compounds of the invention are basic, salts could be prepared in a form of pharmaceutically acceptable salts that will be prepared from nontoxic inorganic or organic acids including but not limited to hydrochloric, hydrobromic, phosphoric, sulfuric, tartaric, citric, acetic, fumaric, alkylsulphonic, naphthalenesulphonic, para-toluenesulphonic, camphoric acids, benzenesulfonic, benzoic, camphorsulfonic, citric, ethanesulfonic, gluconic, glutamic, isethonic, lactic, maleic, malic, mandelic, methanesulfonic, mucic, nitric, pamoic, pantothenic, phosphoric, and succinic.

While it may be possible for the compounds of the invention to be administered as the raw chemical, it is also possible to present them as a pharmaceutical formulation. Accordingly, the present invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. When used in the diagnostic imaging methods of the invention, the compounds of the invention are preferably administered to the patient (e.g., a human) by intravenous injection. The formulations may conveniently be presented in unit dosage form and may be prepared by any of the methods well known in the art of pharmacy. All methods include the step of bringing into association a compound of the present invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds of the invention may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds of the invention may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compounds of the invention may take the form of tablets, lozenges, pastilles, or gels formulated in conventional manner. Such compositions may comprise the active ingredient in a flavored basis such as sucrose and *acacia* or tragacanth.

The compounds of the invention may also be formulated in rectal compositions such as suppositories or retention enemas, e.g., containing conventional suppository bases such as cocoa butter, polyethylene glycol, or other glycerides.

Compounds of the invention may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include solid, liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Via the topical route, the pharmaceutical composition according to the invention may be in the form of liquid or semi liquid such as ointments, or in the form of solid such as powders. It may also be in the form of suspensions such as polymeric microspheres, or polymer patches and hydrogels allowing a controlled release. This topical composition may be in anhydrous form, in aqueous form or in the form of an emulsion. The compounds are used topically at a concentration generally of between 0.001% and 10% by weight and preferably between 0.01% and 1% by weight, relative to the total weight of the composition.

For administration by inhalation, the compounds according to the invention are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example, those suitable for oral administration may include flavoring agents.

The compounds of the invention may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

Compounds according to the invention can be administered at a daily dose of about 0.001 mg/kg to 100 mg/kg of body weight, in 1 to 3 dosage intakes. Further, compounds can be used systemically, at a concentration generally of between 0.001% and 10% by weight and preferably between 0.01% and 1% by weight, relative to the weight of the composition.

The amount of active ingredient that may be combined with the carrier materials to produce a single dosage form will vary depending upon the host treated and the particular mode of administration.

The compounds of the invention can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds of the invention described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for pain involving administration of one of the compounds described herein, increased therapeutic benefit may result by also providing the patient with another therapeutic agent for pain. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the compounds of the invention together with inert or active compounds, or other drugs including wetting agents, flavor enhancers, preserving agents, stabilizers, humidity regulators, pH regulators, osmotic pressure modifiers, emulsifiers, UV-A and UV-B screening agents, antioxidants, depigmenting agents such as hydroquinone or kojic acid, emollients, moisturizers, for instance glycerol, PEG 400, or urea, antiseborrhoeic or antiacne agents, such as S-carboxymethylcysteine, S-benzylcysteamine, salts thereof or derivatives thereof, or benzoyl peroxide, antibiotics, for instance erythromycin and tetracyclines, chemotherapeutic agent, for example, paclitaxel, antifungal agents such as ketoconazole, agents for promoting regrowth of the hair, for example, minoxidil (2,4-diamino-6-piperidinopyrimidine 3-oxide), non-steroidal anti-inflammatory agents, carotenoids, and especially p-carotene, antipsoriatic agents such as anthralin and its derivatives, eicosa-5,8,11,14-tetraynoic acid and eicosa-5,8,11-triynoic acid, and esters and amides thereof, retinoids, e.g., RAR or RXR receptor ligands, which may be natural or synthetic, corticosteroids or oestrogens, alpha-hydroxy acids and a-keto acids or derivatives thereof, such as lactic acid, malic acid, citric acid, and also the salts, amides or esters thereof, or p-hydroxy acids or derivatives thereof, such as salicylic acid and the salts, amides or esters thereof, ion-channel blockers such as potassium-channel blockers, or alternatively, more particularly for the pharmaceutical compositions, in combination with medicaments known to interfere with the immune system, anticonvulsant agents include, and are not limited to, topiramate, analogs of topiramate, carbamazepine, valproic acid, lamotrigine, gabapentin, phenytoin and the like and mixtures or pharmaceutically acceptable salts thereof. A person skilled in the art will take care to select the other compound(s) to be added to these compositions such that the advantageous properties intrinsically associated with the compounds of the invention are not, or are not substantially, adversely affected by the envisaged addition.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, methods for treating diseases, disorders, conditions, or symptoms in a patient (e.g., a human or animal) in need of such treatment are presented herein, the methods comprising the step of administering to the patient an amount of a compound of the invention effective to reduce or prevent the disease, disorder, condition, or symptom, in combination with at least one additional agent for the treatment of said disorder that is known in the art.

EXAMPLES

In a related aspect, therapeutic compositions having at least one novel compound of the invention described herein can be administered in combination with one or more additional agents for the treatment of any of the diseases, disorders, conditions, or symptoms described herein.

It is understood that the foregoing examples are merely illustrative of the present invention. Certain modifications of the articles and/or methods employed may be made and still achieve the objectives of the invention. Such modifications are contemplated as within the scope of the claimed invention. In said examples to follow, all parts and percentages are given by weight, unless otherwise indicated.

Example 1. Compound Preparation (WT13-12)

A combination therapy of the invention that includes 50% w/v L-Arginine, 20% v/v undecylenic acid, and 0.25% w/v *Rheum Officinale* extract was prepared for in vitro and in vivo testing. In one embodiment, the combination therapy further contains 1% Menthol by volume (extract 1 mL of solution and add 0.890 g of Menthol).

To Prepare 200 mL of WT13-12:
1. Aliquot 200 mL of distilled water into a beaker that is on a hot plate.
2. Heat the water to 65° C. and mix with a magnetic stirbar.
3. Add 100 g of L-Arginine to the water slowly until it is all dissolved.
4. Prepare 40 mL of undecylenic acid and 4 g of CreamMaker CA-20 in a separate beaker.
5. Aliquot 200 mL of the L-Arginine solution into a new beaker and add 0.5 g of *Rheum Officinale*. Maintain at 65° C. while spinning.
6. Aliquot 160 mL of the L-Arginine/*Rheum Officinale* Solution into the beaker containing 40 mL of undecylenic acid and 4 g of CreamMaker CA-20.
7. Spin and heat the new solution between 45° C. and 65° C. (50° C. is preferred) until the undecylenic acid and CreamMaker CA-20 goes completely into solution.
8. Once undecylenic acid and CreamMaker CA-20 has gone completely into solution, continue stirring and heating, and extract 2 mL from the solution.
9. Add 1.8 g of menthol to the solution and continue to spin and heat until it goes completely into solution.
10. Allow product to cool and aliquot into storage containers.

Solubility

The individual components (i.e., L-Arginine, undecylenic acid, and *Rheum Officinale* extract) exhibit different solubility characteristics that make the preparation of a therapeutic compound (e.g., a topical cream) difficult or impossible. For example, the inventors found that the following combinations were insoluble in water:
1. L-Arginine is insoluble in water at 50% w/v.
2. Undecylenic acid is insoluble in water at 20% v/v.
3. *Rheum Officinale* extract is insoluble in water at 0.25% w/v.

Furthermore, the inventors found that paired combinations of these components were also insoluble:

1. The combination of L-Arginine and undecylenic acid with the Cream-Maker/water vehicle solution is insoluble.
2. The combination of *Rheum Officinale* extract (0.25% w/v) and L-Arginine (50% w/v) in is insoluble in water.
3. The combination of *Rheum Officinale* extract (0.25% w/v) and undecylenic acid (20% v/v) is insoluble in the Cream-Maker/water vehicle solution.

Only when all three components were combined in the above-specified concentrations was a Cream-Maker/water solution achieved.

Example 2. Broad In-Vitro Bacterial Growth Inhibition

In vitro testing was conducted to measure the efficacy of WT13-12 at inhibiting the growth of clinically relevant bacteria. WT13-12 consists of 500 mg/mL L-arginine, 20% v/v undecylenic acid, and 0.25% w/v *Rheum Officinale*. WT13-12 was streaked across half of a sheep blood agar (SBA) plate and allowed to dry for 15 minutes. The other side was streaked with the vehicle but not containing WT13-12. After drying, 50 µL of purified bacteria at 100,000 col/mL was streaked onto the control and treated sides of the sheep blood agar plates. After streaking, the plates were incubated at 37° C. for 48 hours. Growth was assessed at 24 and 48 hours post-inoculation. Percent inhibition was determined by measuring the treated side vs. the control side with the control side set at 100% growth. Plates were also compared to control plates that were not streaked with the vehicle to ensure the vehicle did not inhibit growth of the microorganisms (vehicle did not inhibit growth).

Figure 2:
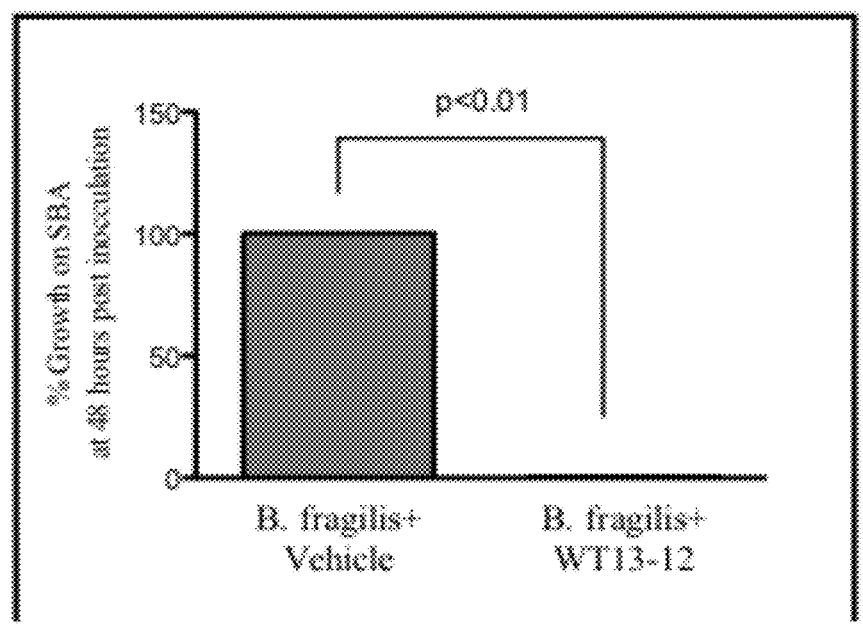
FIG. 2 is a bar graph showing the in vitro growth inhibition of *B. fragilis* by WT13-12 forty-eight hours after inoculation. Screening in cooked meat media showed WT13-12 completely inhibited the growth of *B. fragilis*. All data was compared to vehicle in an unpaired, two-tailed T-test. n=4 tubes per group.
Figure 3:
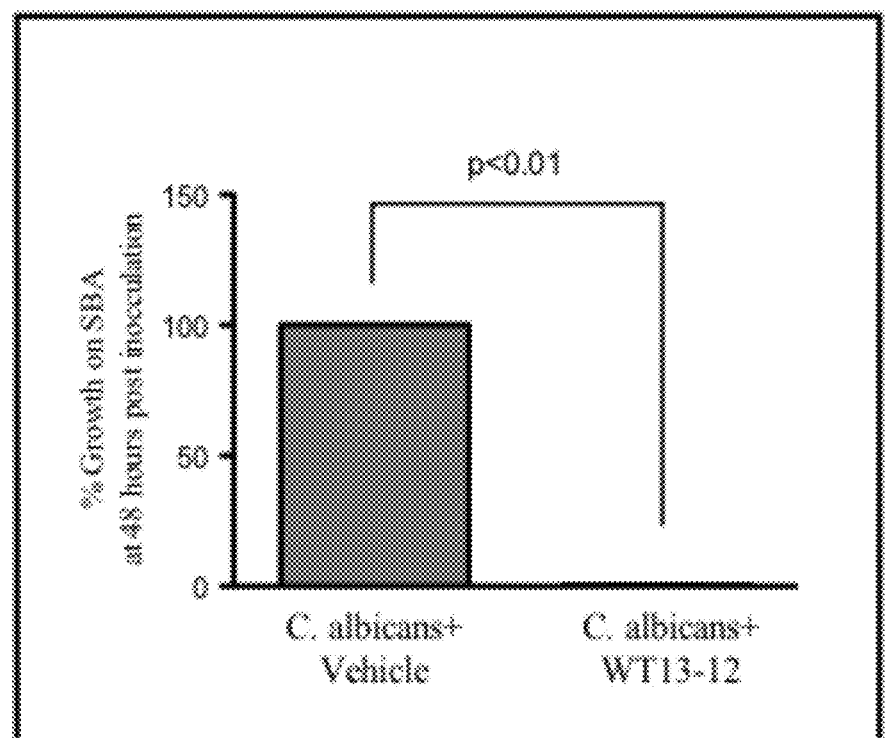
FIG. 3 is a bar graph showing the in vitro growth inhibition of *C. albicans* by WT13-12 forty-eight hours after inoculation. Screening on SBA plates showed WT13-12 completely inhibited the growth of *C. albicans*. All data was compared to vehicle in an unpaired, two-tailed T-test. n=4 test plates per group.
Figure 4:
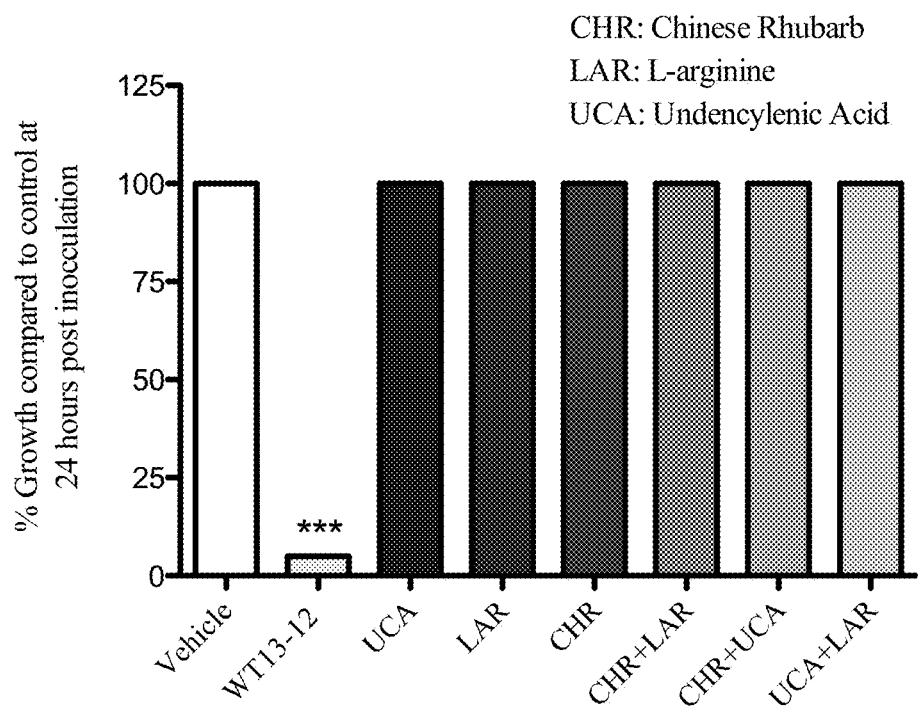
FIG. 4 is a bar graph showing the in vitro growth inhibition of MRSA, versus control, twenty-four hours after inoculation when incubated with WT13-12, undecylenic acid (UCA) alone, L-Arginine (LAR) alone, *Rheum Officinale* extract (CHR) alone, and double combinations of each. Screening on SBA plates showed WT13-12 significantly inhibited the growth of MRSA. The constitutive molecules had no effect on the growth of MRSA when applied individually or in double combinations. All data was obtained by comparing growth a control group to the treatment groups. Each treatment was compared to the vehicle in a one-way ANOVA Tukey's post-hoc. n=4 test plates per group. ***=$p<0.001$.
Figure 5:
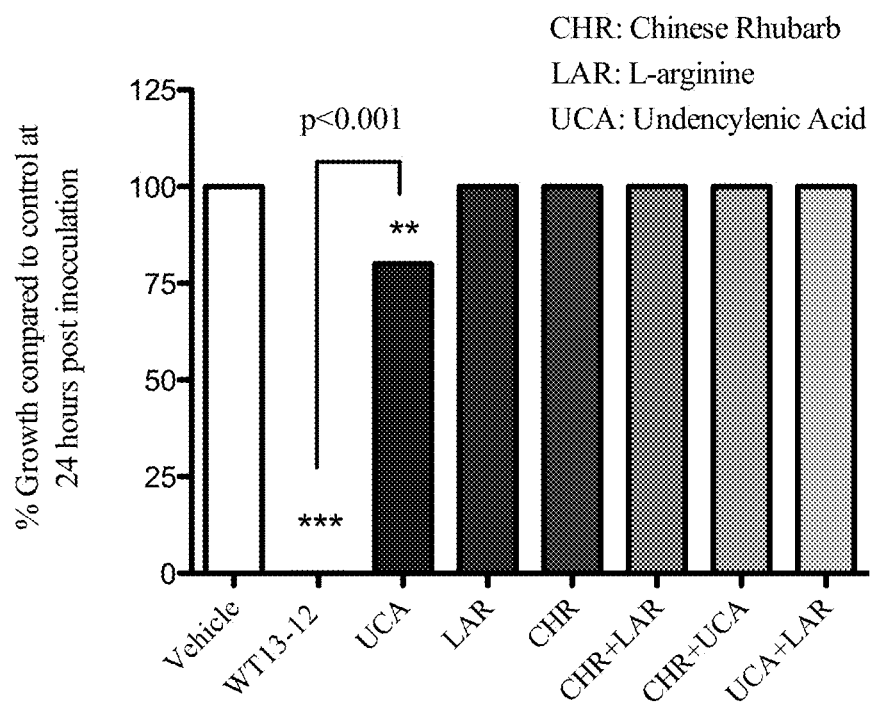
FIG. 5 is a bar graph showing the in vitro growth inhibition of *Streptococcus agalactiae* (Group B beta strep), versus control, twenty-four hours after inoculation when incubated with WT13-12, undecylenic acid (UCA) alone, L-Arginine (LAR) alone, *Rheum Officinale* extract (CHR) alone, and double combinations of each. Screening on SBA plates showed WT13-12 completely inhibited the growth of *S. agalactiae*. Of the constitutive molecules, only UCA had a significant effect on the growth of *S. agalactiae*, however WT13-12 was significantly more effective than UCA at inhibiting growth. All data was obtained by comparing growth a control group to the treatment groups. Each treatment was compared to the vehicle in a one-way ANOVA Tukey's post-hoc. n=4 test plates per group. =$p<0.01$, *=$p<0.001$.
Figure 6:
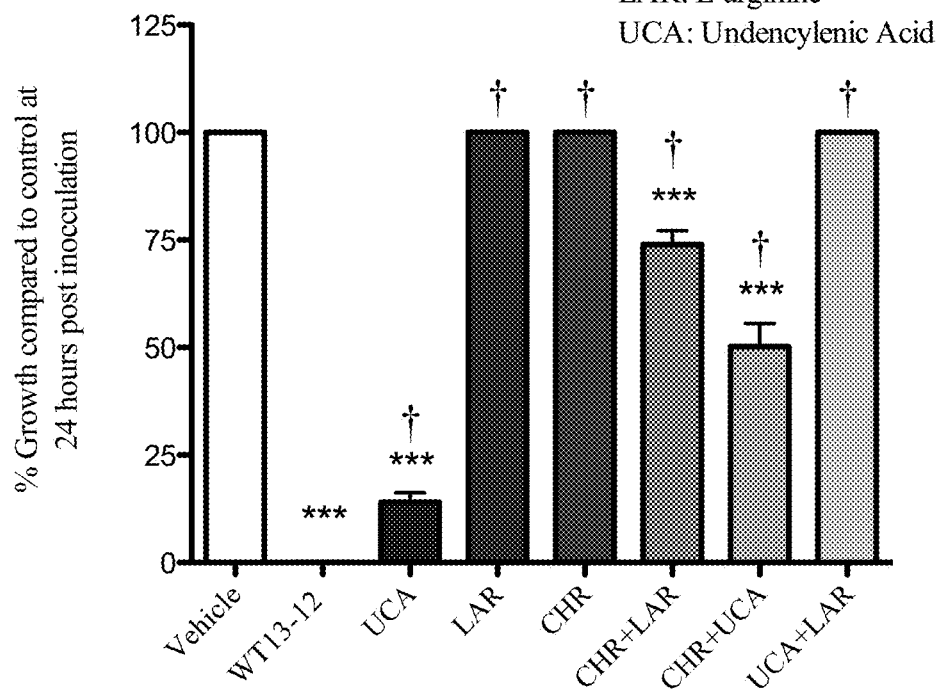
FIG. 6 is a bar graph showing the in vitro growth inhibition of *Streptococcus pyogenes* (Group A beta hemolytic strep), versus control, twenty-four hours after inoculation when incubated with WT13-12, undecylenic acid (UCA) alone, L-Arginine (LAR) alone, *Rheum Officinale* extract (CHR) alone, and double combinations of each. Screening on SBA plates showed WT13-12 completely inhibited the growth of *S. pyogenes*. Of the constitutive molecules, UCA alone, CHR+LAR, and CHR+UCA had significant inhibitory effects on the growth of *S. pyogenes*. WT13-12 was significantly more effective at inhibiting growth. All data was obtained by comparing growth a control group to the treatment groups. Each treatment was compared to the vehicle in a one-way ANOVA Tukey's post-hoc. n=4 test plates per group. ***=$p<0.001$ vehicle vs. groups; †=$p<0.01$ WT13-12 vs. groups.
Figure 7:
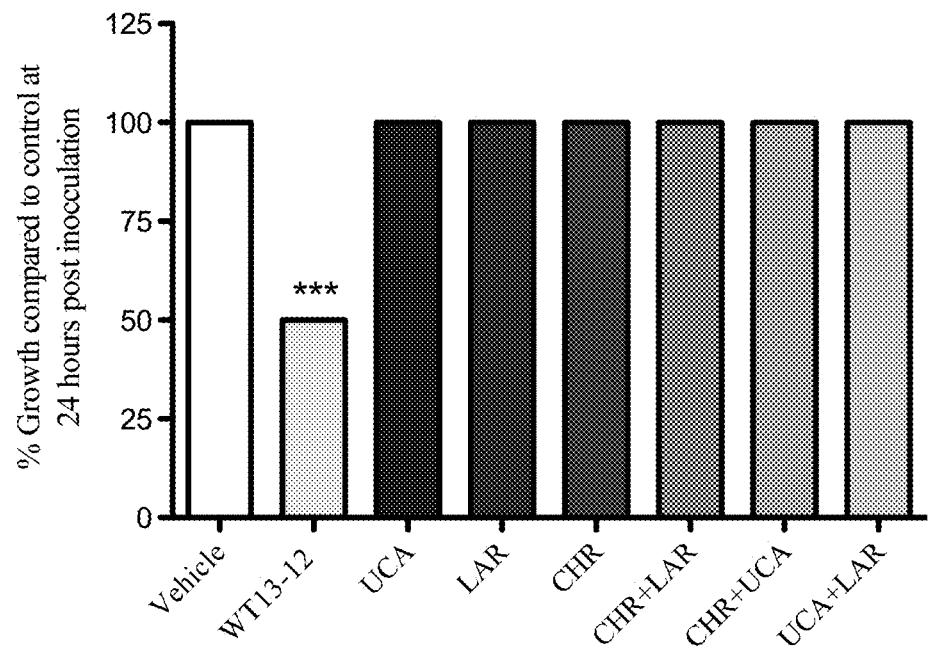
FIG. 7 is a bar graph showing the in vitro growth inhibition of *Enterococcus faecalis* (Group D *enterococcus*), versus control, twenty-four hours after inoculation when incubated with WT13-12, undecylenic acid (UCA) alone, L-Arginine (LAR) alone, *Rheum Officinale* extract (CHR) alone, and double combinations of each. Screening on SBA plates showed WT13-12 significantly inhibited the growth of *E. faecalis*. All other combinations showed no inhibitory effect on growth. All data was obtained by comparing growth a control group to the treatment groups. Each treatment was compared to the vehicle in a one-way ANOVA Tukey's post-hoc. n=4 test plates per group. ***=$p<0.001$ vehicle vs. groups.

FIG. 1 shows compound WT13-12 significantly inhibited the growth of purified Gram-positive bacteria on blood agar plates. Methicillin resistant *staphylococcus aureus* (MRSA), *S. pyogenes* and *S. pneumoniae* were all completely inhibited by WT13-12. *E. faecalis* and *S. agalactiae* were partially inhibited by the compound (30% and 48%, respectively). Testing of WT13-12 on two clinically relevant Gram-negative rods (*E. coli* and *K. pneumoniae*) showed WT13-12 had no effect on growth rates (data not shown). This finding suggests the compound does not have an inhibitory effect on aerobic Gram-negative rods. However, adding 10 mg of WT13-12 into cooked meat media completely inhibited the growth of the Gram-negative anaerobe, *B. fragilis* (FIG. 2). This finding suggests WT13-12 may significantly inhibit certain anaerobic species that typically colonize wounds and surgical sites. We also conducted testing using the yeast species *C. albicans*. Using the same methodology for testing our bacterial cultures, we found that WT13-12 completely inhibited the growth of *C. albicans* at both 24 and 48 hours (FIG. 3).

Example 3. In Vitro Combination Assays Reveal Synergistic Mechanism of Action Each component of WT13-12 was tested individually or in paired combination in the in vitro bacterial growth inhibition assay described above to determine the relative contribution of each component. As shown in FIGS. 4-7, no individual component (i.e., L-Arginine, undecylenic acid, or *Rheum Officinale* extract) or paired combination of components produced any significant inhibition of MRSA, *S. agalactiae, S. pyogenes*, or *E. faecalis* within twenty-four hours following culture inoculation whereas the triple combination WT13-12 restricted culture growth in a statistically significant manner. These results indicate the combination therapy WT13-12 is based on the synergistic mechanism of biological action of its three components and is not simply the result of additive inhibition by the constitutive molecules of the combination therapy.

Example 4. In Vivo Combination Treatment Attenuates MRSA Infection in Rats

Figure 8:
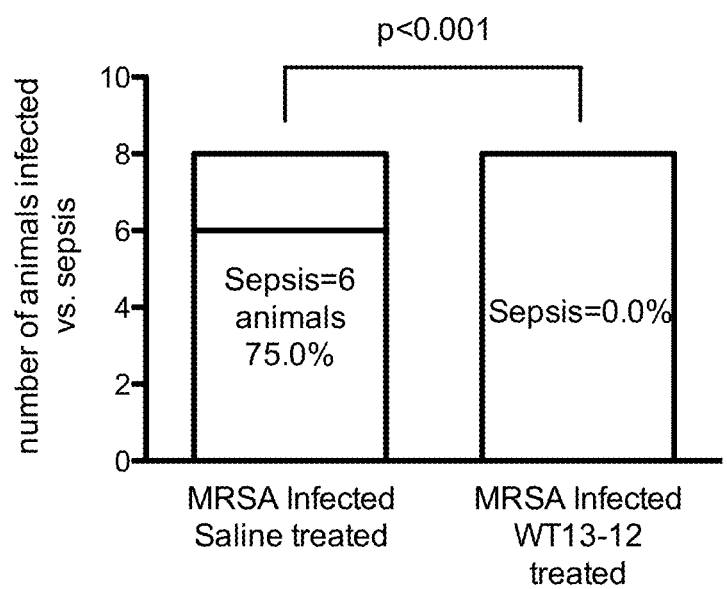
FIG. 8 is a bar graph showing the in vivo reduction of MRSA sepsis in rats (*Rattus norvegicus*, strain: Sprague-Dawley) treated with WT13-12. Of the eight saline treated, MRSA-infected animals, six animals (75.0%) had MRSA-positive blood cultures within four days post-infection. One of the eight animals required early euthanization due to acute sepsis and multi-organ failure. Conversely, of the eight infected animals treated with WT13-12, none had positive blood cultures. Two-tailed T-test. n=8
Figure 9:
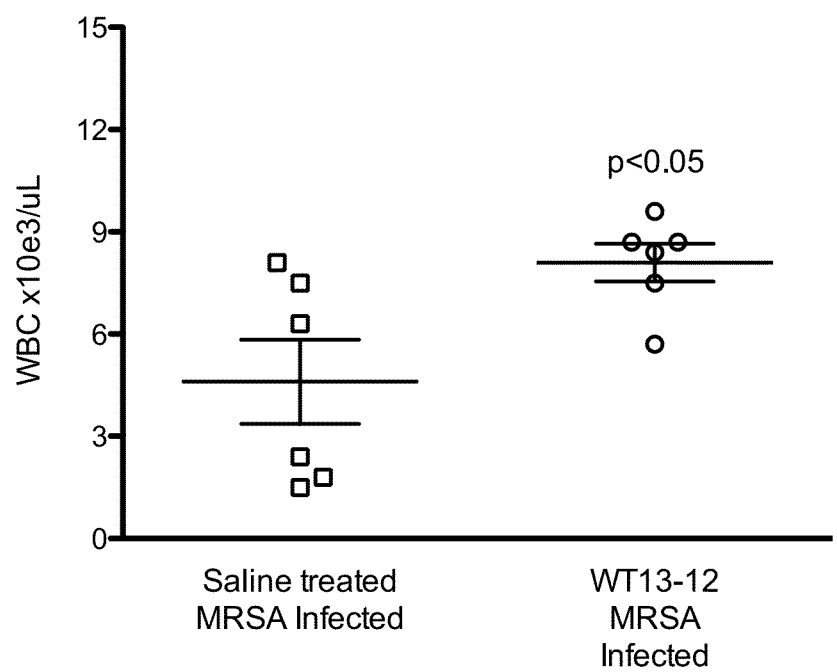
FIG. 9 is a bar graph showing the in vivo reduction of MRSA-induced neutropenia in rats treated with WT13-12. Saline treated, MRSA-infected animals had severe neutropenia (WBC<3) in three out of the seven animals. One saline treated animal that suffered acute septicemia had a WBC count of 32 and was excluded as a high physiological outlier. All of the WT13-12 treated animals had WBC counts in the normal range (5.5-12).
Figure 10:
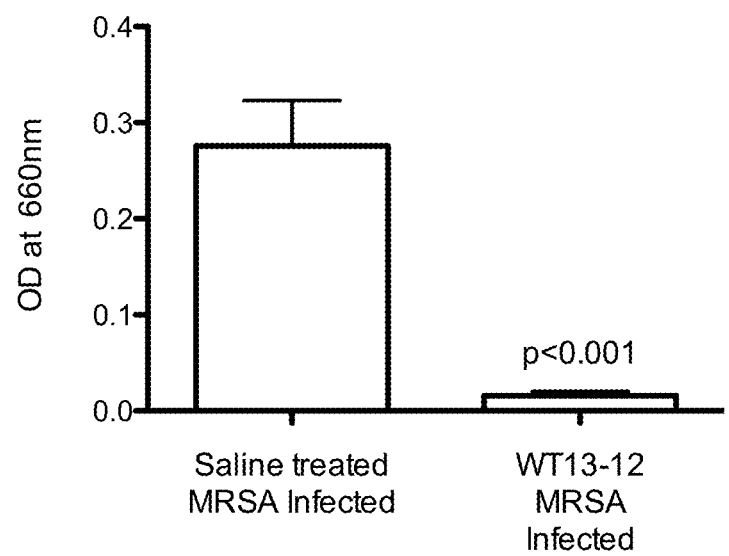
FIG. 10 is a bar graph showing the reduction of MRSA-induced dead tissue, bacteria, and cellular debris in rats treated with WT13-12. As each wound was opened the tissue was swabbed and then swirled in 3 mL of sterile broth. The broth was then read spectrophotometrically to objectively assess the cleanliness of the wound. The higher the optical density (OD) at 660 nm the greater the amount of dead tissue, bacteria, and cellular debris in the solution, indicating a "dirty wound." Treatment with WT13-12 significantly reduced ($p<0.001$) the amount of dead tissue, bacteria, and cellular debris in the wound. This effect was further verified by performing a visual inspection. Saline treated tissue, in all cases, had at least one abscess present. In contrast, none of the WT13-12 animals had abscesses present. Necrotic tissue patches (soft, black patches of tissue) were also present in all saline treated wounds and absent in all WT13-12 treated wounds. Unpaired two-tailed T-test, n=8.

Sixteen anaesthetized adult male rats received a 2.5 cm surgical wound on the right, lateral back area. The wounds were intentionally infected with 100,000 colonies/mL methicillin-resistant *S. aureus* (MRSA). Four hours after infection, WT13-12 soaked gauze or saline soaked gauze was packed into the wound. Twenty-four hours later the packing was removed, the wound swabbed for culture, and the wound repacked with treated or saline gauze. This procedure was repeated on day three post-infection. On day four post-infection the animal was swabbed again, euthanized, and blood was drawn for cultures and analysis. As shown in FIGS. 8-10, WT13-12 significantly attenuated an active MRSA wound infection in rats. Treatment with WT13-12 completely blocked the development of sepsis in all animals. Of the eight saline treated infected animals, six were found to have MRSA in their blood. If we had continued this study for a longer period than four days, it is quite possible the other two animals would have developed sepsis as well. Wound structure and integrity was vastly different between the WT13-12 treated and the saline treated animals. Treatment with WT13-12 significantly reduced the amount of dead tissue, bacteria, and cellular debris in the wound. This effect was further verified by performing a visual inspection. Saline treated tissue, in all cases, had at least one abscess present. In contrast, none of the WT13-12 animals had abscesses present. Necrotic tissue patches (soft, black patches of degraded tissue) were also present in all saline treated wounds and absent in all WT13-12 treated wounds. White blood cell counts indicate that all of the WT13-12 treated animals were not undergoing an active immune response, indicating they were not fighting an active infection. In contrast, three of the saline treated animals had severe neutropenia indicating a clear inability to mount an effective immune response. One saline treated animal that suffered acute sepsis had an extremely high white count indicating end stage infection. This bi-phasic WBC response to infection occurs commonly in MRSA sepsis. As the bacteria grow and multiply in the blood stream, circulating WBC levels are depleted as they fight the infection. As the bacteria levels continue to increase and overwhelm the immune system, WBC's increase concurrently as an adaptive response.

Example 5. In-Vivo Testing: Case Study 1

A 38-year old female with a 24-year history of cystic acne presented with several deep facial acne patches. The affected areas were swollen and inflamed and measured approximately five mm in diameter. The patient was screened to ensure no other medications were being taken. A selected area was treated with WT13-12 and covered with an adhesive strip for eight hours. Treatment was administered for 5 consecutive days. After the second day of treatment the swelling and inflammation decreased significantly. By the fifth day the diameter of the acne lesion decreased to <0.5 mm. The untreated acne lesion increased to 7 mm. One week after treatment with WT13-12 ended, the lesion was completely healed. The untreated acne lesion remained unchanged and was present 21 days after the beginning of the assessment period. The treated area showed no scarring or residual effect from the treatment.

Example 6. In-Vivo Testing: Case Study 2

A 36-year old female presented with 12 mm boil on the left buttock. The area was swollen, inflamed, and sensitive to pressure. Laboratory culture of the wound site grew a pure culture of Group B beta *streptococcus*. WT13-12 was applied and covered with adhesive strips for 24 hours. At the end of this period the adhesive strips were removed, the area was cleaned with soap and assessed. The inflammation and swelling was visually reduced. At the onset of treatment the patient reported an immediate decrease in pain at the infection site. Twenty-four hours post-treatment the patient had no discomfort from the boil. Five days after treatment the boil was no longer visible. The treated area showed no scarring or residual effect from the treatment.

Example 7. In-Vivo Testing: Case Study 3

A 9 year old male presented with an active Tinea corpus (ringworm) infection measuring 20 mm in diameter. The infected site was treated with WT13-12 and covered with adhesive strips for eight hours. The patient reported an immediate cessation in the "itchiness" of the infection site. Treatment was continued for four days. Forty-eight hours after treatment was initiated the ringworm infection had decreased significantly. Ten days after treatment began the infection was no longer visible.

Example 8. In-Vivo Testing: Case Study 4

A 39 year old male presented with an active Tinea corpus (ringworm) infection on the right forearm. The infection site measured 10 mm in diameter. The infected site was treated with WT13-12 and covered with adhesive strips for eight hours. The patient reported a "tingling sensation" with an absence of pain. Treatment was continued for four days. Forty-eight hours after treatment was initiated the ringworm infection had decreased to 4 mm. Seven days after treatment began the infection was no longer visible.

All Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Other embodiments are within the claims.

What is claimed is:

1. A therapeutic composition for treating a microbial infection comprising:
   L-Arginine or a pharmaceutically acceptable salt thereof in amount between 5% w/v to 50% w/v,
   undecylenic acid or a pharmaceutically acceptable salt thereof in an amount between 2% w/v to 50% w/v, and
   an extract of *Rheum Officinale* in an amount between 0.025% w/v to 2.5 w/v.

2. The composition of claim 1, wherein the amount of L-Arginine is about 50% w/v, the amount of undecylenic acid is about 20% v/v, and the amount of the extract of *Rheum Officinale* is about 0.25% w/v.

3. The composition of claim 1 further comprising a cooling or heating additive.

4. The composition of claim 3, wherein said cooling additive is menthol.

5. The composition of claim 1 in combination with a pharmaceutically acceptable excipient, diluent, or carrier.

6. The composition of claim 5, wherein said excipient, diluent, or carrier is optimized for topical application.

7. A method for treating a microbial infection in a subject in need thereof, the method comprising administering to a said subject a therapeutically effective amount of a composition comprising:
   L-Arginine in amount between 5% w/v to 50% w/v,
   undecylenic acid in an amount between 2% w/v to 50% w/v, and
   an extract of *Rheum Officinale* in an amount between 0.025% w/v to 2.5 w/v.

8. The method of claim 7, wherein the amount of L-Arginine is about 50% w/v, the amount of undecylenic acid is about 20% v/v, and the amount of the extract of *Rheum Officinale* is about 0.25% w/v.

9. A kit comprising (i) the therapeutic composition of claim 2; and (ii) instructions for utilizing said composition.

* * * * *